US00PP33858P2

(12) United States Plant Patent
Van Swieten

(10) Patent No.: US PP33,858 P2
(45) Date of Patent: Jan. 11, 2022

(54) ***PHALAENOPSIS* ORCHID PLANT NAMED 'PHALINCE'**

(50) Latin Name: ***Phalaenopsis* hybrid**
Varietal Denomination: PHALINCE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,549

(22) Filed: Aug. 11, 2021

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALINCE', particularly characterized by having white flowers with greenish-yellow and white lips, flowers with a flat shape in lateral view, dorsal sepals with an incurving curvature of the longitudinal axis, long whiskers, and is propagated by meristem tissue culture, is disclosed.

3 Drawing Sheets

Genus and species: *Phalaenopsis* hybrid.
Variety denomination: 'PHALINCE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALINCE'.

The new *Phalaenopsis* plant is a product of a planned breeding program conducted by the inventor in Bleiswijk, the Netherlands. The objective of this breeding program was to create a new *Phalaenopsis* plant with attractive white flowers with greenish-yellow and white lips, suitable for potted plant production.

The new *Phalaenopsis* plant 'PHALINCE' is a result of cross-pollination made by the inventor in August 2012 in Bleiswijk, the Netherlands, of the proprietary female, or seed parent, *Phalaenopsis* hybrid '01-4030' (unpatented) with the proprietary male, or pollen parent, *Phalaenopsis* hybrid '21232-01' (unpatented).

The new *Phalaenopsis* was selected by the inventor as a single plant within the progeny of the stated cross-pollination in a controlled greenhouse in Bleiswijk, the Netherlands, in June 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0295), by Applicant who obtained the subject matter disclosed directly from the inventor. 'PHALINCE' has not been made publicly available or sold anywhere in the world prior to the effective filing date of this application with the exception of sales or disclosures made one year or less before the effective filing date of this claimed invention by Applicant who obtained 'PHALINCE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALINCE' as a new and distinct variety of *Phalaenopsis* plant:

1) White flowers with greenish-yellow and white lips;
2) Flower shape in lateral view is flat;
3) Curvature of longitudinal axis of dorsal sepal is incurving; and
4) Whiskers are long.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in March 2021. Colors in the photographs may differ from the color values cited in the detailed botanical description, which accurately describe the actual colors of the new variety.

DESCRIPTION OF THE NEW VARIETY

Figure 1:
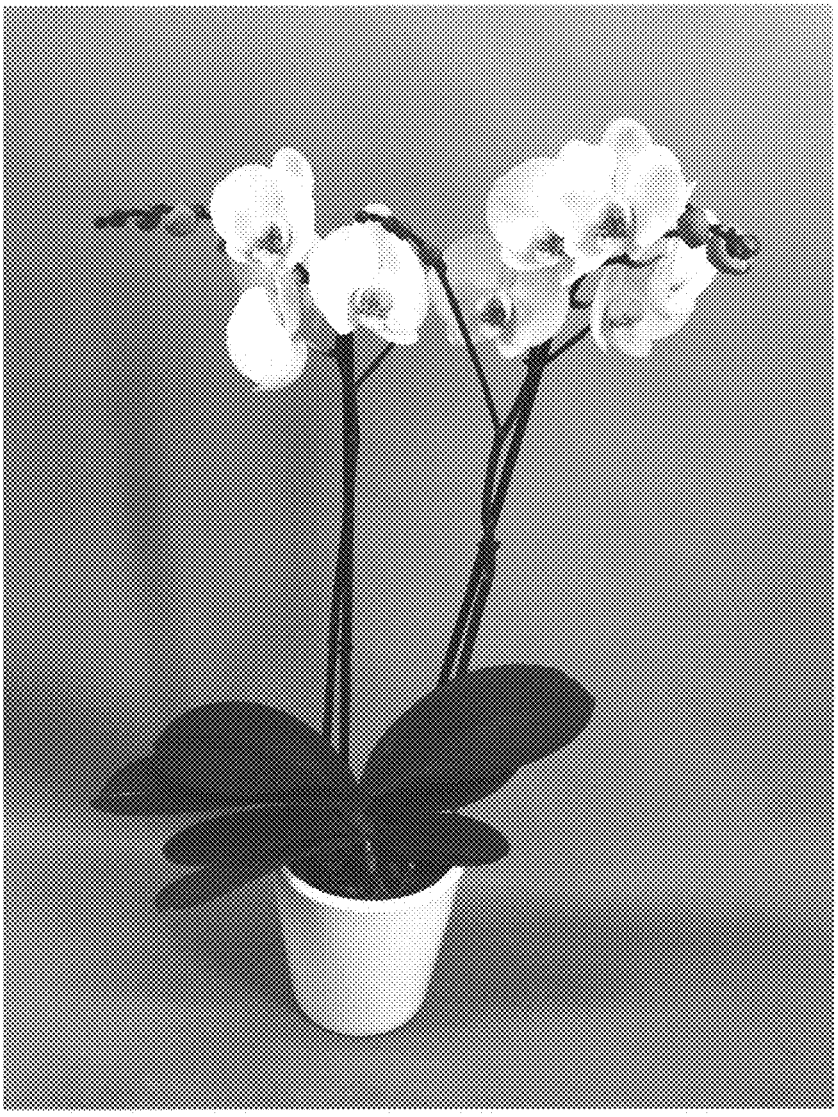
FIG. 1 shows the overall plant habit, including blooms, buds, and foliage of 'PHALINCE'.
Figure 2:
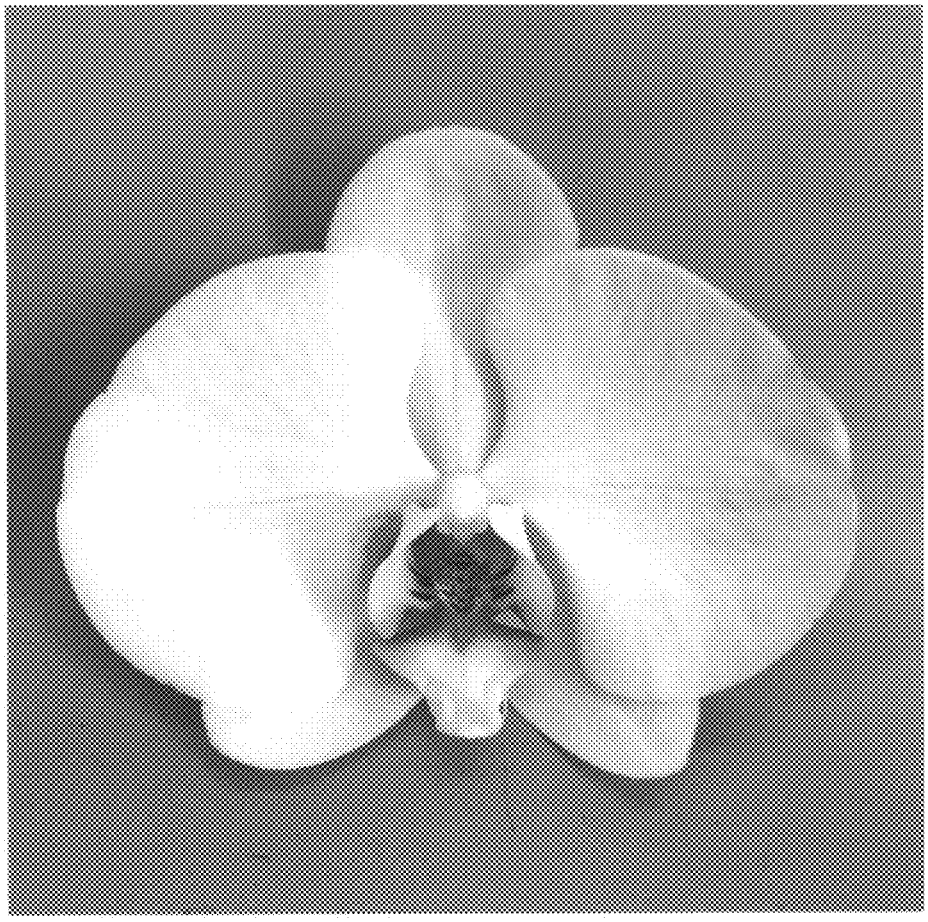
FIG. 2 shows a close-up of a flower of 'PHALINCE'.
Figure 3:
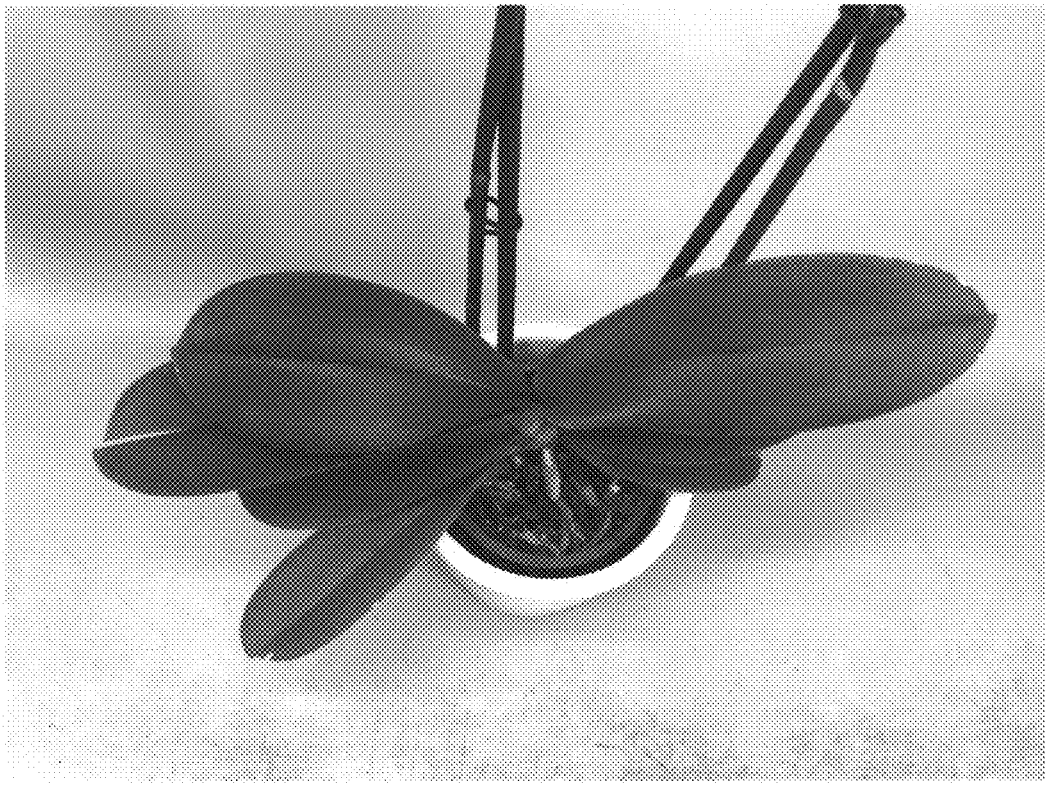
FIG. 3 shows an overhead view of the leaves of 'PHALINCE'.

The following detailed description sets forth the distinctive characteristics of 'PHALINCE'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALINCE'.

Parentage:

*Female parent*.—*Phalaenopsis* cultivar '01-4030' (unpatented).

*Male parent*.—*Phalaenopsis* cultivar '21232-01' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 144C) with a touch of purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 55.0 cm to 60.0 cm.

*Width* (*measured from leaf tips*).—About 36.0 cm to 38.0 cm.

*Vigor*.—Strong.

Leaves:

*Mature leaves*.—Quantity per plant: 8 to 10 leaves are produced before flowering. Length (fully expanded): 18.0 cm to 20.0 cm. Width: 7.0 cm to 8.0 cm. Position of the broadest part of the leaf: Toward the tip. Shape: Obovate. Base shape: Moderately elongated. Apex: Obtuse asymmetric. Leaf blade angle with the petiole (measured from the horizontal position): Between 10 degrees and 30 degrees. Leaf margin: Entire. Color: Upper surface: RHS 146A. Lower surface: RHS 146B. Texture (both upper and lower surfaces): Smooth. Thickness: 2.6 mm to 2.8 mm. Variegation: Absent. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—12 to 16.

*Length*.—55.0 cm to 60.0 cm.

*Diameter*.—6.0 mm to 7.0 mm.

*Strength*.—Strong.

*Aspect*.—Upright to slightly pendent.

*Texture*.—Smooth.

*Color*.—Mix of green (RHS 146B) and brown (RHS 200A).

*Internode length*.—2.5 cm to 3.5 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 220.0 mm to 270.0 mm.

*Flowering time*.—First flowers can be expected 10 to 11 months after planting in a 12-cm pot.

*Flower*.—Height: 78.0 mm to 83.0 mm. Diameter: 90.0 mm to 95.0 mm. Depth of lip: 24.0 mm to 26.0 mm.

*Flower longevity*.—On the plant: 11 to 13 weeks.

*Flower shape*.—Flat.

*Fragrance*.—Absent.

*Flower bud*.—Average size: Large. Length: 25.0 mm to 27.0 mm. Width: 21.0 mm to 23.0 mm. Shape: Egg shaped. Color: Light yellow-green (a color in between RHS 145B and RHS 145C) with a touch of diluting purplish-red (RHS N77B) toward the tip.

*Petals*.—Arrangement: Open/free. Shape: Semi-circular. Apex: Emarginated asymmetric. Margin: Weakly undulated. Length (from base to tip): 39.0 mm to 41.0 mm. Width: 52.0 mm to 54.0 mm. Position of the broadest part of the petal: Toward the base. Color (when fully opened): Upper surface: Basic color: White (RHS NN155C). Over color: Absent. Lower surface: Basic color: White (RHS NN155C). Over color: Touch of light yellow-green (RHS 145D) and very light purple midvein (RHS 76B). Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 45.0 mm to 47.0 mm. Width: 29.0 mm to 31.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Touch of very light purple (RHS 76B) and light yellow-green (RHS 145D). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse asymmetric. Margin: Entire. Length (from base to tip):

45.0 mm to 47.0 mm. Width: 26.0 mm to 28.0 mm. Position of the broadest part of the lateral sepals: Toward the base. Color (when fully opened): Upper surface: Basic color: White (RHS NN155C). Over color: Touch of light yellow-green (RHS 145C) and dotted (RHS 72A) at the base. Lower surface: Basic color: White (RHS NN155C). Over color: Light yellow-green (RHS 145C). Number of spots, dots, and stripes on the lateral sepals (upper surface): Few to medium small dots. Color of spots, dots, and stripes on the lateral sepals (upper surface): RHS 72A. Density of netting of the lateral sepals (upper surface): None. Color of the netting (upper surface): Not applicable.

*Labellum* (*lip*).—Whiskers: Present. Length of whiskers: 18.0 mm to 20.0 mm. Color of whiskers: White (RHS NN155C) with light yellow-green tips (RHS 2C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 19.0 mm to 22.0 mm. Width: 15.0 mm to 17.0 mm. Color: Upper surface: Purplish-red stripes (RHS 71A) at the base; greenish-yellow (RHS 151C) on one side toward margin; white (RHS NN155C) toward the other margin and tip. Lower surface: Greenish-yellow (RHS 151C) and white (RHS NN155C) toward the other margin and tip. Number of spots and stripes on the lateral lobe: Few stripes. Color of spots and stripes on the lateral lobe: RHS 71A. Density of netting of the lateral lobe: None. Color of the netting: Not applicable.

*Apical lobe*.—Shape: Triangular. Margin: Entire. Length: 24.0 mm to 26.0 mm. Width: 22.0 mm to 24.0 mm. Color: Upper surface: Red margin (RHS 176A) and greenish-yellow (RHS 151C) at the base and at wings; white (RHS NN155C) toward whiskers; greenish-yellow midvein (RHS 4A). Lower surface: Red margin (RHS 176A) and greenish-yellow (RHS 151D) at the base and at wings; white (RHS NN155C) toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Large. Height: 8.0 mm to 9.0 mm. Length: 6.0 mm to 7.0 mm. Width: 4.0 mm to 5.0 mm. Color: Light greenish-yellow (RHS 4B) on sides; yellow tips (RHS 13A); spotted (RHS 175A).

Reproductive organs:

*Column*.—Length: 7.0 mm to 9.0 mm. Diameter: 6.0 mm to 7.0 mm. Color: White (RHS NN155C).

*Pollinia*.—Quantity: 2. Diameter: 0.8 mm to 1.0 mm. Color: Orange (RHS 25A).

*Ovary*.—Length: 9.0 mm to 11.0 mm. Diameter: 2.1 mm to 2.5 mm.

*Pedicel*.—Length: 29.0 mm to 31.0 mm. Diameter: 2.6 mm to 2.9 mm. Color: Hint of brown (RHS N199A) at the base; light yellow-green (RHS 145B); light yellow-green (RHS 145C) and touch of very light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALINCE', cultivar '01-4030' (unpatented), is no longer in existence, therefore a meaningful comparison cannot be made.

'PHALINCE' differs from the male parent plant '21232-01' (unpatented) in that 'PHALINCE' has medium curvature of the lateral lobe and moderately elongated leaf bases, whereas '21232-01' has weak curvature of the lateral lobe and moderately to very elongated leaf bases.

'PHALINCE' is most similar to the commercial *Phalaenopsis* plants named 'PHALFOWIC' (U.S. Plant Pat. No. 29,245) and 'PHALFUBNE' (U.S. Plant Pat. No. 30,395). 'PHALINCE' differs from the commercial variety 'PHALFOWIC' in that 'PHALINCE' has emarginated dorsal sepal apexes, whereas 'PHALFOWIC' has obtuse dorsal sepal apexes. Additionally, 'PHALINCE' has shorter whiskers than 'PHALFOWIC'.

'PHALINCE' differs from the commercial variety 'PHALFUBNE' in that 'PHALINCE' has obtuse leaf apexes and emarginated dorsal sepal apexes, whereas 'PHALFUBNE' has rounded leaf apexes and obtuse dorsal sepal apexes. Additionally, 'PHALINCE' has smaller flowers and shorter whiskers than 'PHALFUBNE'.

I claim:

1. A new and distinct variety of *Phalaenopsis* plant named 'PHALINCE', substantially as described and illustrated herein.

* * * * *